US010828507B2

(12) United States Patent
Ribbing et al.

(10) Patent No.: US 10,828,507 B2
(45) Date of Patent: Nov. 10, 2020

(54) CLINICAL DECISION SUPPORT (CDS) FOR RADIOTHERAPY IN PROSTATE CANCER

(71) Applicant: KONINKLIJKE PHILIPS N.V., Eindhoven (NL)

(72) Inventors: Carolina Ribbing, Aachen (DE); Katrin Bitter, Tuebingen (DE)

(73) Assignee: Koninklijke Philips N.V., Eindhoven (NL)

( * ) Notice: Subject to any disclaimer, the term of this patent is extended or adjusted under 35 U.S.C. 154(b) by 703 days.

(21) Appl. No.: 14/770,482

(22) PCT Filed: Mar. 7, 2014

(86) PCT No.: PCT/IB2014/059526
§ 371 (c)(1),
(2) Date: Aug. 26, 2015

(87) PCT Pub. No.: WO2014/147509
PCT Pub. Date: Sep. 25, 2014

(65) Prior Publication Data

US 2016/0008629 A1 Jan. 14, 2016

Related U.S. Application Data

(60) Provisional application No. 61/803,479, filed on Mar. 20, 2013.

(51) Int. Cl.
*G01N 33/48* (2006.01)
*A61N 5/10* (2006.01)
*G01N 33/68* (2006.01)
*H01J 49/00* (2006.01)
*G06F 19/00* (2018.01)

(52) U.S. Cl.
CPC ......... *A61N 5/103* (2013.01); *G01N 33/6848* (2013.01); *G01N 33/6893* (2013.01); *H01J 49/0027* (2013.01); *G01N 2800/40* (2013.01); *G01N 2800/52* (2013.01); *G06F 19/3481* (2013.01)

(58) Field of Classification Search
None
See application file for complete search history.

(56) References Cited

U.S. PATENT DOCUMENTS 8,221,984 B2 7/2012 Fung et al.
8,929,625 B2 1/2015 Ribbing et al.
2002/0142343 A1 10/2002 Hutchens et al.
2003/0207462 A1 11/2003 Kitagawa
2012/0290324 A1 11/2012 Ribbing et al.
2013/0034868 A1* 2/2013 Liao .................. G01N 33/6893 435/7.92
2014/0113388 A1 4/2014 Bitter et al.

FOREIGN PATENT DOCUMENTS

WO WO 2010109357 A1 * 9/2010 ............... A61N 5/10
WO WO 2010/136942 * 12/2010 ............ G06F 19/00

OTHER PUBLICATIONS

Pietrowska et al., Mass spectrometry-based analysis of therapy-related changes in serum proteome patterns of patients with early-stage breast cancer, Journal of Translational Medicine 8:66, 2010, pp. 1-11. (Year: 2010).*
Feng et al., Identification of Biomarkers for Predicting Nasopharyngeal Carcinoma Response to Radiotherapy by Proteomics, Cancer Res: 70(9), May 1, 2010, pp. 3450-3462. (Year: 2010).*
Wei, J.T. "Development and Validation of the Expanded Prostate Cancer Index Composite (EPIC) for Comprehensive Assessment of Health-Related Quality of Life in Men with Prostate Cancer". Urology 56 (6), 2000, pp. 899-905.
Hutchens, T.W. et al. "New Desorption Strategies for the Mass Spectrometric Analysis of Macromolecules". Rapid Communications in Mass Spectrometry, vol. 7, pp. 576-580 (1993).
Petricoin, E.F. et al. "Use of proteomic patterns in serum to identify ovarian cancer". Lancet, vol. 359, pp. 572-577, Feb. 16, 2002.
Adam, B-L et al. "Serum Protein Fingerprinting Coupled with a Pattern-matching Algorithm Distinguishes Prostate Cancer from Benign Hyperplasia and Healthy Men". Cancer Research, vol. 62, pp. 3609-3614, Jul. 1, 2002.
Semmes, O.J. et al. "Evaluation of Serum Protein Profiling by Time-of-Flight Mass Spectrometry for the Detection of Prostate Cancer: I. Assessment of Platform Reproducibility". Clinical Chemistry, vol. 1, pp. 102-112 (2005).
Espina, V. et al. "Use of proteomic analysis to monitor responses to biological therapies". Expert Opin Ther, vol. 1, pp. 83-93 (2004).
Carr, S. et al., "The need for guidelines in publication of peptide and protein identification data—working group on publication guidelines for peptide and protein identification data", Molecular & Cellular Proteomics, American Society for Biochemistry and Molecular Biology, US, vol. 3, No. 6, Jun. 1, 2004, pp. 531-533.

* cited by examiner

*Primary Examiner* — Gary Counts

(57) ABSTRACT

A system (30) and method for detecting or predicting toxicity induced by radiation therapy. A device (34) is configured for determining polypeptide biomarkers present in a urine sample. At least one processor (36) is programmed to detect or predict radiation toxicity based on one or more polypeptide biomarkers determined to be in the urine sample.

7 Claims, 9 Drawing Sheets

| | LT | HT | LT | HT | | | |
|---|---|---|---|---|---|---|---|
| M/Z AVG | 6,733.15 | 6,733.06 | | | HT: N=7, LT: N=10 | Time point 1 (0 GY) | BOWEL TOXICITY |
| IAVG | 40.96 | 10.53 | | | | | |
| ISTD | 24.60 | 5.12 | | | | | |
| D | 74.3 | | | | | | |
| P | 0.02 | | | | | | |
| CV | 82.94 | | | | | | |
| ROC | 0.19 | | | | | | |
| M/Z AVG | 6,731.35 | 6,732.69 | 2,862.56 | 2,863.04 | HT: N=6, LT: N=6 | Time point 2 (20-26 GY) | |
| IAVG | 23.12 | 27.09 | 11.18 | 23.94 | | | |
| ISTD | 14.15 | 20.25 | 6.38 | 25.46 | | | |
| D | -17.16 | | -114.0 | | | | |
| P | 0.87 | | 0.63 | | | | |
| CV | 64.29 | | 105.90 | | | | |
| ROC | 0.56 | | 0.56 | | | | |
| M/Z AVG | 6,733.17 | 6,731.29 | 2,863.03 | 2,862.84 | HT: N=8, LT: N=9 | Time point 3 (40-46 GY) | |
| IAVG | 24.12 | 16.63 | 7.02 | 28.69 | | | |
| ISTD | 17.09 | 15.89 | 3.56 | 18.02 | | | |
| D | 31.0 | | -308.6 | | | | |
| P | 0.21 | | 0.03 | | | | |
| CV | 79.98 | | 95.91 | | | | |
| ROC | 0.19 | | 0.79 | | | | |
| M/Z AVG | 6,733.88 | 6,732.64 | 2,862.41 | 2,862.98 | HT: N=6, LT: N=10 | Time point 4 (60-66 GY / 70-76 GY) | |
| IAVG | 44.30 | 26.77 | 10.06 | 14.16 | | | |
| ISTD | 21.39 | 24.87 | 6.35 | 14.06 | | | |
| D | 39.6 | | -40.7 | | | | |
| P | 0.05 | | 0.83 | | | | |
| CV | 83.11 | | 97.33 | | | | |
| ROC | 0.20 | | 0.58 | | | | |
| M/Z AVG | 6,732.71 | 6,730.79 | 2,862.37 | 2,862.44 | HT: N=7, LT: N=10 | Time point 5 (60-66 GY / 70-76 GY) | |
| IAVG | 25.79 | 29.66 | 7.27 | 25.40 | | | |
| ISTD | 13.51 | 21.30 | 5.43 | 26.00 | | | |
| D | -15.04 | | -249.3 | | | | |
| P | 0.92 | | 0.17 | | | | |
| CV | 61.73 | | 129.67 | | | | |
| ROC | 0.48 | | 0.69 | | | | |

FIG. 1

| FIG. 3-I |
| --- |
| FIG. 3-II |

FIG. 3

| URINARY TOXICITY | | | LT | HT | LT | HT | LT | HT | LT | HT | LT | HT |
| --- | --- | --- | --- | --- | --- | --- | --- | --- | --- | --- | --- | --- |
| Time point 1 (0 GY) | HT: N=4, LT: N=10 | M/Z AVG | 10,566.02 | 10,572.09 | 8,839.63 | 8,841.83 | 8,291.55 | 8,290.59 | 6,716.42 | 6,716.33 | 4,478.19 | 4,478.63 |
| | | IAVG | 16.24 | 6.84 | 48.83 | 23.03 | 28.09 | 15.22 | 22.73 | 8.20 | 26.03 | 25.65 |
| | | ISTD | 6.40 | 4.41 | 20.48 | 15.54 | 8.27 | 10.99 | 16.67 | 4.79 | 7.51 | 8.18 |
| | | D | 57.9 | | 52.8 | | 45.8 | | 63.9 | | 1.4 | |
| | | P | 0.05 | | 0.07 | | 0.05 | | 0.1 | | 1.0 | |
| | | CV | 52.74 | | 52.16 | | 41.54 | | 80.58 | | 27.82 | |
| | | ROC | 0.15 | | 0.20 | | 0.15 | | 0.20 | | 0.5 | |
| Time point 2 (20-26 GY) | HT: N=2, LT: N=8 | M/Z AVG | 10,572.16 | 10,584.88 | 8,845.03 | 8,838.55 | 8,293.28 | 8,294.02 | 6,717.11 | 6,719.44 | 4,478.59 | 4,478.29 |
| | | IAVG | 15.49 | 7.46 | 48.69 | 29.20 | 24.24 | 15.04 | 27.47 | 14.17 | 23.72 | 52.63 |
| | | ISTD | 5.40 | 5.29 | 17.21 | 10.37 | 10.13 | 2.77 | 20.34 | 3.41 | 11.26 | 6.88 |
| | | D | 51.8 | | 40.0 | | 38.0 | | 48.4 | | -121.9 | |
| | | P | 0.07 | | 0.19 | | 0.19 | | 0.6 | | 0.07 | |
| | | CV | 41.87 | | 37.92 | | 14.28 | | 71.67 | | 56.46 | |
| | | ROC | 0.09 | | 0.22 | | 0.22 | | 0.38 | | 0.94 | |

| URINARY TOXICITY | | | | | | | | | | |
|---|---|---|---|---|---|---|---|---|---|---|
| **Time point 3 (40-46 GY) — HT: N=5, LT: N=10** | | | | | | | | | | |
| M/Z AVG | 10,564.58 | 10,566.32 | 8,839.82 | 8,828.66 | 8,292.41 | 8,290.75 | 6,714.14 | 6,710.19 | 4,478.74 | 4,477.99 |
| IAVG | 17.92 | 8.26 | 53.69 | 30.14 | 27.76 | 13.49 | 23.50 | 14.57 | 21.94 | 40.63 |
| ISTD | 7.96 | 5.85 | 17.94 | 11.68 | 7.47 | 11.10 | 19.40 | 11.30 | 5.78 | 17.47 |
| D | 53.9 | | 43.9 | | 51.4 | | 38.0 | | -58.2 | |
| P | 0.02 | | 0.01 | | 0.03 | | 0.6 | | 0.02 | |
| CV | 58.01 | | 42.42 | | 47.51 | | 84.02 | | 49.17 | |
| ROC | 0.14 | | 0.08 | | 0.14 | | 0.38 | | 0.92 | |
| **Time point 4 (60-66 GY / 70-76 GY) — HT: N=4, LT: N=7** | | | | | | | | | | |
| M/Z AVG | 10,570.79 | 10,571.08 | 8,843.06 | 8,842.43 | 8,294.26 | 8,292.20 | 6,718.96 | 6,719.25 | 4,477.43 | 4,478.08 |
| IAVG | 20.01 | 13.07 | 53.71 | 30.52 | 26.46 | 18.71 | 24.34 | 15.83 | 19.11 | 43.80 |
| ISTD | 12.52 | 12.57 | 15.99 | 27.49 | 10.40 | 18.37 | 9.44 | 17.43 | 6.88 | 13.16 |
| D | 34.7 | | 43.2 | | 29.3 | | 36.0 | | -129.1 | |
| P | 0.5 | | 0.2 | | 0.26 | | 0.3 | | 0.01 | |
| CV | 78.39 | | 57.62 | | 52.95 | | 78.21 | | 47.28 | |
| ROC | 0.36 | | 0.21 | | 0.27 | | 0.27 | | 0.98 | |
| **Time point 5 (60-66 GY / 70-76 GY) — HT: N=4, LT: N=9** | | | | | | | | | | |
| M/Z AVG | 10,568.29 | 10,571.17 | 8,842.24 | 8,843.04 | 8,294.00 | 8,292.14 | 6,717.27 | 6,719.87 | 4,478.10 | 4,477.70 |
| IAVG | 18.59 | 6.24 | 65.97 | 18.01 | 27.13 | 9.99 | 30.75 | 8.30 | 24.69 | 32.84 |
| ISTD | 8.27 | 3.27 | 34.49 | 11.36 | 11.30 | 5.36 | 15.48 | 5.25 | 9.85 | 15.19 |
| D | 66.4 | | 72.7 | | 63.2 | | 73.0 | | -33.0 | |
| P | 0.01 | | 0.01 | | 0.05 | | 0.03 | | 0.17 | |
| CV | 67.25 | | 71.51 | | 57.11 | | 69.58 | | 43.53 | |
| ROC | 0.00 | | 0.06 | | 0.17 | | 0.11 | | 0.71 | |

FIG. 3-II

CLINICAL DECISION SUPPORT (CDS) FOR RADIOTHERAPY IN PROSTATE CANCER

CROSS-REFERENCE TO PRIOR APPLICATIONS

This application is the U.S. National Phase application under 35 U.S.C. § 371 of International Application No. PCTT/IB2014/059526, filed on Mar. 7, 2014, which claims the benefit of U.S. Provisional Application No. 61/803,479, filed on Mar. 20, 2013. These applications are hereby incorporated by reference herein.

The present application relates generally to clinical decision support. It finds particular application in conjunction with radiotherapy (RT) and will be described with particular reference thereto. However, it is to be understood that it also finds application in other usage scenarios and is not necessarily limited to the aforementioned application.

In RT, radiation is applied to a target structure, such as a tumor, containing cancerous or malignant tissue. In so doing, certain parts of healthy tissue are exposed to and damaged by the radiation. RT planning seeks to provide a sufficiently high dose to the target structure, while keeping doses to the healthy tissue and critical structures, such as the bowel and the bladder, as low as possible. However, one problem with known RT planning is that it is typically made without input on the radiosensitivity of the individual patients. During the course of RT, some patients react with severe side effects on doses that cause little side effects in others.

For example, RT of prostate cancer often causes severe acute and late side effects, such as toxicity of the bowel and the urinary tract, which have a severe influence on the patient's health-related quality of life (QoL). To measure health-related QoL among men with prostate cancer, the Expanded Prostate cancer Index Composite (EPIC) was developed. It assesses the disease-specific aspects of prostate cancer and its therapies, and comprises four summary domains: urinary, bowel, sexual and hormonal. The higher the EPIC score, the better the health-related QoL is.

The present application provides a new and improved system and method which overcome the above-referenced problems and others.

In accordance with one aspect, a method for detecting or predicting toxicity induced by radiation therapy is provided. A urine sample is received from a subject. Radiation toxicity is detected or predicted using one or more biomarkers within the urine sample, wherein each biomarker corresponds to a polypeptide.

In accordance with another aspect, a system for detecting or predicting toxicity induced by radiation therapy is provided. The system includes a device configured for determining polypeptide biomarkers present in a urine sample. The system further includes at least one processor programmed to detect or predict radiation toxicity based on one or more polypeptide biomarkers determined to be in the urine sample.

In accordance with another aspect, biomarkers for detecting or predicting toxicity induced by radiation therapy are provided. The biomarker include polypeptides specific to toxicity induced by radiation. The polypeptides include masses of 4478±9 Da, 6716±13 Da, 8293±17 Da, 8840±18 Da, 10571±21 Da, 2863±6 Da or 6732±13 Da.

One advantage resides in informed individual side-effect assessment and prediction.

Another advantage resides in more reliable (in terms of sensitivity and specificity) side effect assessment and prediction. The prediction can be used to help decide on using alternative treatments, avoiding radiation boosts, etc. in extra side-effect prone patients.

Another advantage resides in high throughput.

Another advantage resides in testing automation.

Another advantage resides in non-invasive testing.

Another advantage resides in at home collection of samples, which are stable and easy to transport.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 illustrates two biomarkers experimentally determined for bowel toxicity.

FIGS. 2A and 2B each illustrate intensity differences for a biomarker for bowel toxicity.

FIG. 3 illustrates five biomarkers experimentally determined for urinary toxicity.

FIGS. 4A-E each illustrate intensity differences for a biomarker indicative of urinary toxicity.

Figure 2A:
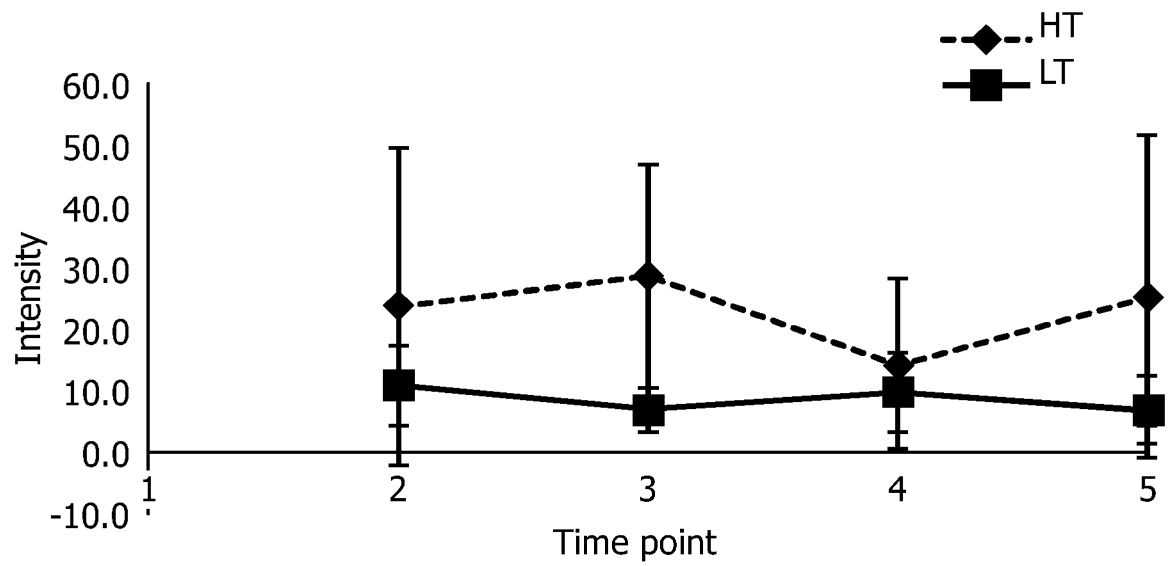

Within molecular diagnostics (MDx), molecular and cellular products are used as disease markers or as pathological fingerprints, which can be used for diagnosis of diseases. One approach to identify molecular and cellular products is mass spectrometry (MS). MS is a method for determining molecular mass, involving sample ionization and transfer to the gas phase. By acceleration in an electric field and separation in a vacuum, molecular ions are separated according to their mass-to-charge ratio (m/z). MS is a good technique for accurate and sensitive analysis of biological species, such as blood serum, urine and lymph containing proteins and peptides.

One approach to ionization is matrix-assisted laser desorption ionization (MALDI). In MALDI, the sample is co-crystallized with a so called matrix. The matrix is an ultraviolet (UV) absorbing aromatic compound which is added to the sample in large excess.

Common UV absorbing matrices include α-cyano-4-hydroxy cinnamic acid (CHCA) and 3,5-dimethoxy-4-hydroxy cinnamic acid (sinapinic acid). A pulsed UV laser supplies the energy for ionization and desorption. The matrix absorbs the UV energy and transfers it to the sample. Typically, a nitrogen ($N_2$) laser with 3.7 electronvolts (eV), a 337 nanometer (nm) wavelength, and 4 nanosecond (ns) pulses is used. In contrast, without the use of a matrix, about 13-14 eV is required for one approximately 12 kilodalton (kDa) molecule to be desorbed and ionized. Using MALDI-MS, molecules with masses exceeding $10^5$ dalton (Da) can be ionized and analyzed without appreciable fragmentation.

In order to prepare a complex sample, such as molecular digests, cell lysates and urine, for MALDI-MS, the complex sample has to be prefractionated in order to eliminate the suppression of molecular desorption and ionization, to avoid sample compositions which are too heterogeneous and to avoid detector overload. Common prefractionation methods include liquid chromatography, electrophoresis, isoelectric focusing, desalting, and removal of particles by centrifugation, as well as concentration or dilution. Often, two-dimensional (2D) gel electrophoresis is performed. Spots of interest are excised from the gel and dissolved for subsequent MALDI-MS analysis. Another common arrangement is liquid chromatography coupled directly to another type of mass spectrometer with electrospray ionization (ESI-MS), corresponding to a low-resolution mass separation in series with a high-resolution mass separation.

Enhancements to MALDI include chromatographic sample prefractionation in surface-enhanced affinity capture (SEAC), surface enhanced laser desorption ionization (SELDI), and covalent binding of matrix to the sample holding plate. Chromatographic media have material properties that make it possible to separate one type of molecule from another (e.g., hydrophobic, hydrophilic, $COO^-$, $NH_3^+$, and so on).

In SELDI, the sample is brought into contact with a chromatographic chip, which binds a subgroup of the sample molecules. For sample preparation, individual chromatographic chips are accommodated in a special holder, a so called bioprocessor, to achieve a standard microtiter plate format.

Unbound molecules are removed by buffer washing, and a MALDI-MS measurement is performed directly off the chromatographic surface. Matrix is either added as a last step before MS measurement, or is already covalently bound to the chip surface. Little or no fragmentation is observed. As an example, when using a hydrophobic surface in SELDI, the subgroup of hydrophobic molecules will be fished out of a complex sample. For biomarker discovery, protein expression profiling, and diagnostic purposes, this is useful for investigation or diagnosis of diseases which lead to a change in the expression of hydrophobic peptides.

SELDI is advantageous because the sample is concentrated directly on a chromatographic surface in a relatively short process with high throughput. The chromatographic MS targets can be automatically loaded with sample, prepared, and analyzed in the mass spectrometer.

From urine, diagnostic mass spectrometric proteomic patterns showing, for example, early cancer or host response to radiation can be obtained. The underlying hypothesis is that pathological changes within an organ are reflected in proteomic patterns in bodily fluids like urine. This is plausible because, generally speaking, every event occurring in the human body is molecularly mediated, mostly by proteins. On-going physiological or pathological events are represented by the relative cellular abundance of tens of thousands of different proteins, along with their chemically modified and cleaved forms. Every cell gives an account of its physiological state in the molecular products it presents and disposes. Proteins and protein fragments actively or passively enter the circulation of blood and lymph perfusing the tissue and a subgroup end up in the urine.

Building on the foregoing, a set of biomarkers which can be used for monitoring, early assessment and prediction of radiotoxicity caused by treatment of prostate cancer are described hereafter. Radiotoxicity is toxicity induced by radiation. Such monitoring, prediction and assessment has typically only been possible based on grading of patient reported side effects, on risk estimates based on prescribed dose, morphological features from medical imaging (e.g., distance from rectum wall to prostate, grade of bowel filling, etc.) or rather complex cell based methods.

To monitor the patient for radiotoxicity and/or assess susceptibility to radiotoxicity, MS proteomic patterns of the biomarkers, which are indicative of radiotoxicity or susceptibility, are matched to a urine sample of the patient. In contrast to standard diagnostic procedures, which are based on only one biomarker detected by, for example, so called enzyme-linked immunosorbent assay (ELISA) antibody assays, MS proteomic patterns consist of combinations of several individual biomarkers. This advantageously allows more reliable (in terms of sensitivity and specificity) monitoring and assessment. Although, it is to be appreciated that the biomarkers can be used for production of antibodies by identifying the proteins behind the MS peaks of the biomarkers. Such antibodies can be used for molecular imaging, histology staining or ELISA antibody assays. These ELISA assays can then be used to monitor the collection of biomarkers which were identified by MS as decisive for, for example, radiotoxicity.

While the set of biomarkers are directed towards radiotoxicity of prostate cancer patients, the set of biomarkers can be employed for patients with other diseases, such as bladder, rectum, endometrial or cervix cancer. Further, the monitoring and the early assessment of radiotoxicity can be performed together with monitoring of multiple diseases using a single MS scan of the urine sample by applying different MS proteomic patterns of the biomarkers for each of the diseases.

Biomarker concentrations can additionally be combined with data from, for example, medical imaging, disease and/or patient specific information, such as genetic data, tumor grade and stage, and co-morbidities to obtain even more reliable predictions. The biomarker concentrations can also be employed to compute a “toxicity index” for each patient. The toxicity index can be displayed to the planning physician in a radiation therapy planning system to indicate whether the patient is apt for an extra radiation boost or if extra low dose limits have to be applied to the organs at risk due to high individual radiosensitivity. The toxicity index can, for example, be displayed as a traffic light symbol or with colour coding of organs at risk.

The set of biomarkers were experimentally determined from the urine samples of 23 ectomized prostate cancer patients with high and low bowel and urinary toxicity. For each patient, five urine samples from five consecutive time points were collected. Time point 1 corresponds to a time point before radiation therapy (i.e., 0 gray (Gy)). Time points 2-4 correspond to time points during radiation therapy at 20-26 Gy, 40-46 Gy and 60-66 Gy, respectively. These urine samples were collected the morning after radiation therapy. Time point 5 corresponds to a time point two months after radiation therapy. The urine samples were collected by the patients at home and brought on ice to a lab, where they were centrifuged at 4000 revolutions per minute (RPM) and 4 degrees Celsius (° C.), aliquoted and frozen at −80° C.

To each of the urine samples, a toxicity severity was assigned using expanded prostate cancer index composite (EPIC) sheets filled out by the corresponding patient at the corresponding point in time. EPIC assesses the side-effect level of prostate cancer radiotherapy, and comprises four summary domains: urinary, bowel, sexual and hormonal. As will be seen, the toxicity severity is hereafter employed to classify biomarkers as discriminators of low bowl toxicity and high bowl toxicity, as well as low urinary toxicity and high urinary toxicity.

Because the protein concentration of urine varies within a very large interval, the protein concentration of every urine sample was measured and the sample diluted with water to a concentration of 0.0251 grams/liter (g/L) to make the samples comparable. MS data sets describing the spectra of biomarkers within the diluted urine samples were then acquired using SELDI-MS. The MS data sets were analyzed to identify patterns indicative of radiotoxicity and/or susceptibility in the form MS peak intensity (corresponding to peptide concentration) at sets of m/z values. Some patient samples were considered in four replicates in order to assess the reproducibility, which was found to be high enough for reliable classification of the small training set.

To acquire the MS data sets using SELDI-MS, the diluted urine samples of each time point were prepared on Protein chip arrays in a bioprocessor. The bioprocessor included 12 chips with 8 spots, each spot for one of the diluted urine samples. The chromatographic chips were part of BIORAD PROTEINCHIP CM10 ARRAYS. Even more, the applied chemicals discussed hereafter correspond to the cleaning grade p.a.

Before applying the samples to the chip arrays, the diluted urine samples were denatured in a 96-well plate. This included adding 60 μL of denaturing buffer U9 (i.e., 9 mole (M) urea, 2% 3-[(3-cholamidopropyl)dimethylammonio]-1-propanesulfonate (CHAPS), 10 millimole (mM) tris(hydroxymethyl)aminomethane (TRIS), pH 9, stored at −80° C.) into each of the wells. For each of the diluted urine samples, 40 μL of the diluted urine sample was added to a corresponding well. The plate then underwent a vortex for 20 minutes at 4° C. and 600 RPM.

After denaturing the samples, the Protein chip arrays were equilibrated. This included adding 100 μl of binding buffer (i.e., 0.2% nonyl phenoxypolyethoxylethanol (NP40), 100 mM $NH_4Ac$, pH 4.5) to each of the wells. The bioprocessor was then incubated for 5 minutes on a plate shaker at 600 RPM, and the buffer was removed by pouring out and tapping the bioprocessor on a paper towel pile. The foregoing actions of equilibrating were then repeated.

Without drying the chips, the diluted urine samples were added to the bioprocessor and incubated. This included adding 100 μL of binding buffer to the wells and immediately transferring the diluted urine samples into corresponding wells of the bioprocessor. The samples were incubated on a plate shaker for 60 minutes at 600 RPM. The samples were then removed by pouring out and tapping the bioprocessor on paper towel pile. The incubation was repeated twice with fresh samples.

The bioprocessor was then washed. This included adding 150 μl of binding buffer to each of the wells. The binding buffer was left to sit for 5 minutes while being shaken by a plate shaker at 600 RPM. The binding buffer was then discarded and the foregoing was repeated two more times. 150 μl of washing buffer (e.g., 5 mM 4-(2-hydroxyethyl)-1-piperazineethanesulfonic acid (HEPES), pH 7) was added to each of the wells and incubated for 5 seconds. The washing buffer was then discarded and the foregoing was repeated once more. The chips then air dried.

While the chips were drying, a matrix was prepared. This included centrifuging a tube with sinapinic acid (SPA) matrix powder for 2 minutes (i.e., ca 15 k times gravitational acceleration (xg), 2 minutes). Fresh 1% trifluoroacetic acid (TFA) (i.e., 50 μl TFA and 5 ml water) was prepared. 125 μl of acetonitrile (ACN) and 125 μl of 1% TFA were added to the SPA tube. The tube then underwent a vortex for 1 minute, followed by mixing on an Eppendorf shaker at 14000 RPM for 15 minutes. Thereafter, the tube was centrifuged (i.e., ca 15 k xg, 3 minutes) to sediment undissolved matrix and the supernatant was transferred to a new tube. 1 μl of SPA was then added to the dried spots on chips twice, with 10 minutes between the additions to allow for drying.

After preparing the bioprocessor, the chips were inserted in a SELDI mass spectrometer, specifically a BIORAD SELDI-TOF MS PCS4000, and MS data sets were acquired for the diluted urine samples (i.e., the chips of the bioprocessor were analyzed). The acquisition was performed with settings optimized for the low mass range (i.e., the peptide range). Namely, the mass range was set from 2000 to 35000 Da with the focus mass set to 8000 Da. Further, the matrix attenuation was set to 1000 Da, and the sampling rate was set to 400 megahertz (MHz). SELDI quantization was used for acquisition. One warming shot with an energy of 5600 nanojoules (nJ) was set, and 15 data shots with an energy of 4600 nJ were set. No warming shots after spectrum acquisition were set.

After acquisition, the MS data sets (the spectra) of the diluted urine samples were analyzed using BIORAD PROTEIN CHIP SOFTWARE, VERSION 3.5. In a first pass, peaks with signal-to-noise ratio (SNR) >5 and a valley depth of 0.3 were automatically detected. The minimum peak threshold was set to 15.0% of all spectra. All first pass peaks were preserved. The cluster mass window was set to 0.2% of mass to cluster like peaks across the spectra. In other words, peaks within the mass interval of ±0.2% were clustered. In the second pass, peaks with SNR >2 and a valley depth of 2 were automatically detected. Estimated peaks were added to complete clusters at auto centroid.

Peaks in the mass range 2000-10000 Da were analyzed according to m/z, intensity (I), standard deviation (STD), p-value (P), receiver operating characteristic (ROC)-limit, coefficient of variation (CV) and intensity difference (D), as shown in FIG. 1. The identified clusters show either a p-value≤0.06, a ROC-limit≥0.8 or ≤0.2, or a D≥25. All selected clusters fulfill at least one of these conditions at one time point (i.e., one of time points 1-5). Additionally the minimum cluster intensity (i.e., mean value over all spectra at each time point) had to exceed 1.

Figure 2B:
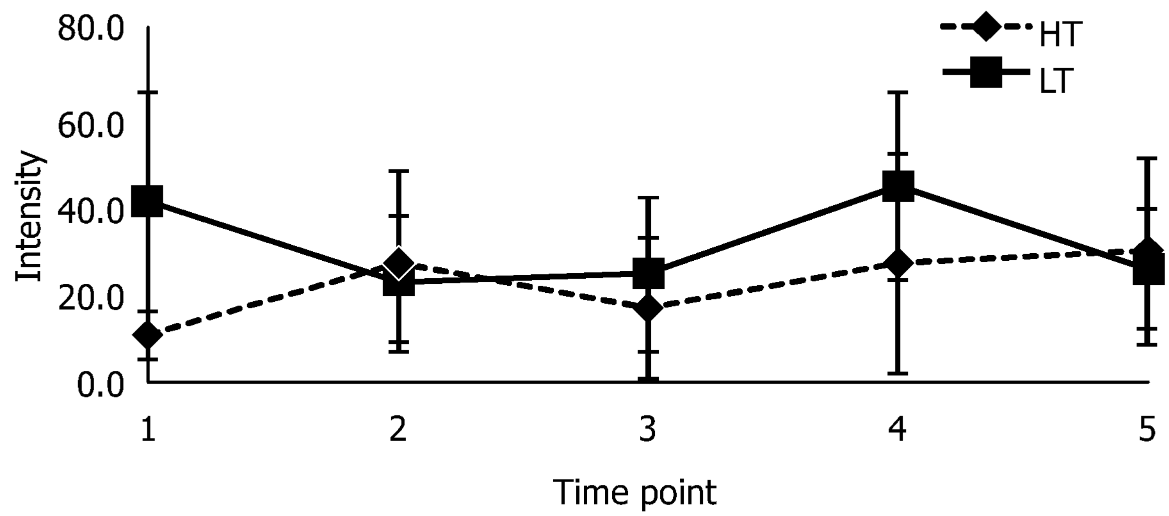

Referring to FIG. 1, two clusters with m/z values of 2863 Da and 6732 Da were identified, cluster 2863 with intensity difference without overlapping standard deviations for high bowel toxicity (HT) versus low bowel toxicity (LT) at time point 3, shown in FIG. 2A, and cluster 6732 with intensity difference without overlapping standard deviations for high bowel toxicity (HT) versus low bowel toxicity (LT) at time point 1, shown in FIG. 2B. Additionally, the 2863 Da and 6732 Da clusters could be distinguished between HT and LT with p-values of 0.03 and 0.02, respectively, and ROC-limits of 0.79 and 0.19, at time point 3 and 1, respectively. Advantageously, the high intensity difference at time point 1 indicates that a radiotoxicity prone patient can be identified before radiation therapy (i.e., the 6732 Da biomarker allows for toxicity prognosis).

Figure 4A:
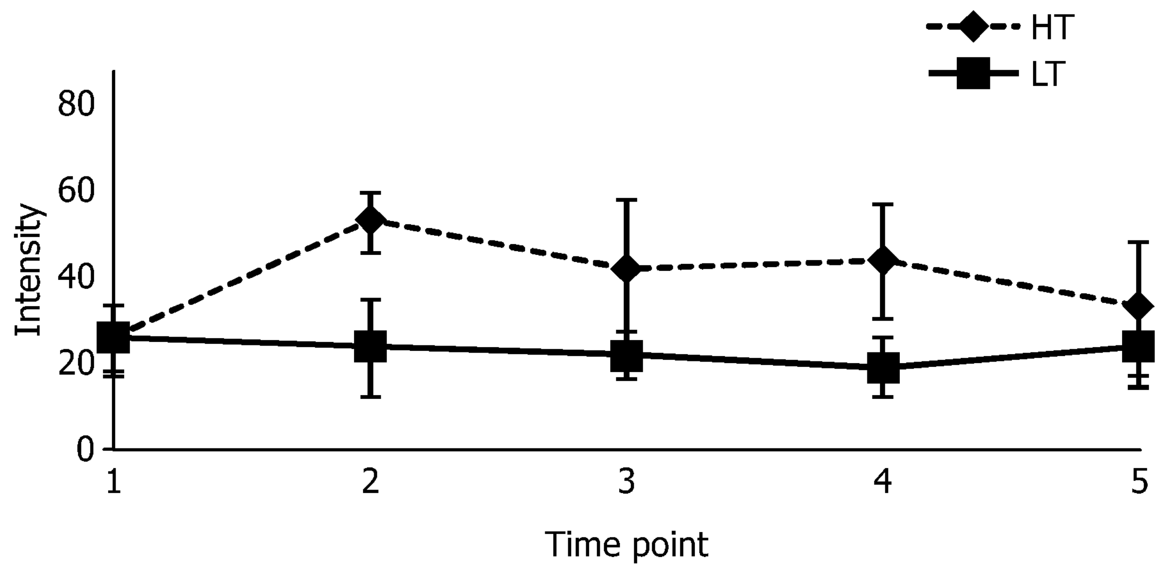
Figure 4B:
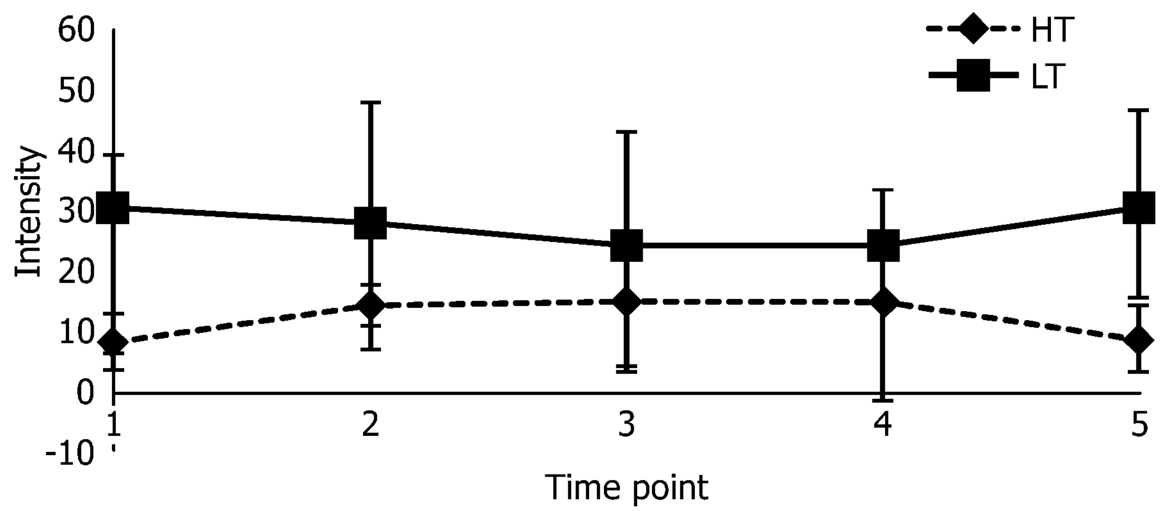
Figure 4C:
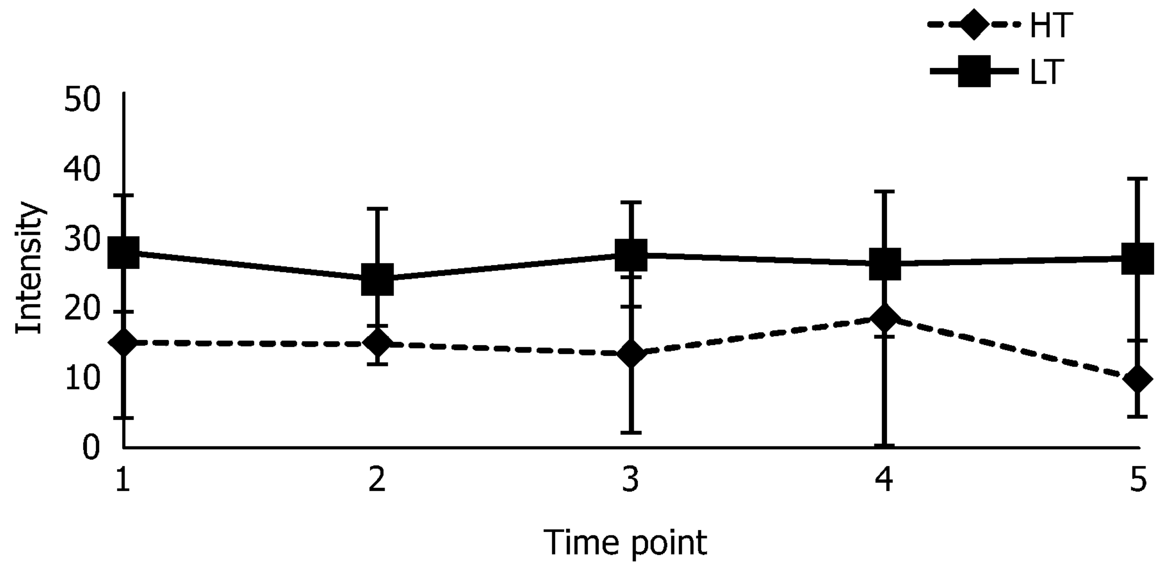
Figure 4D:
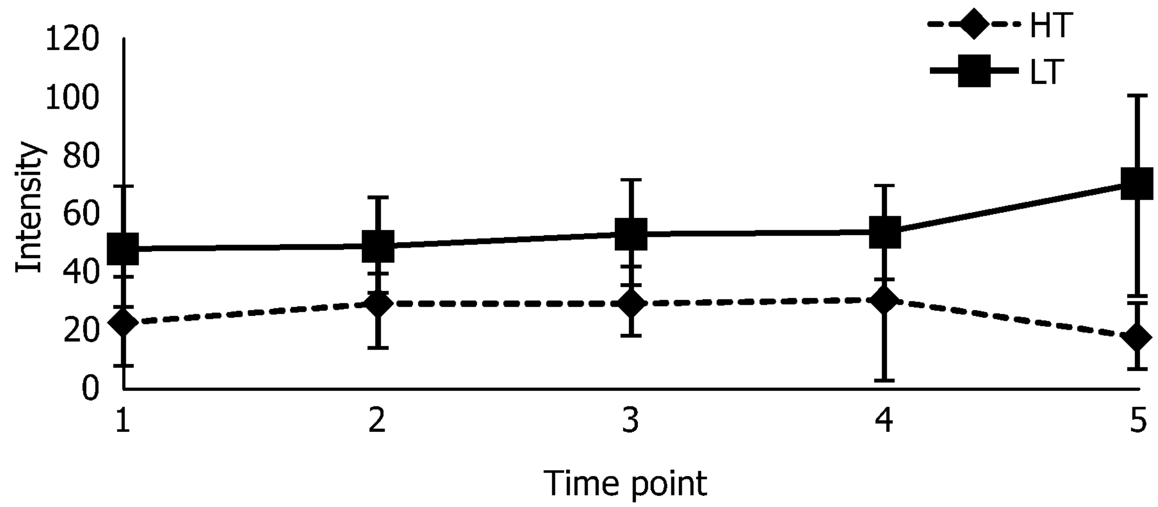
Figure 4E:
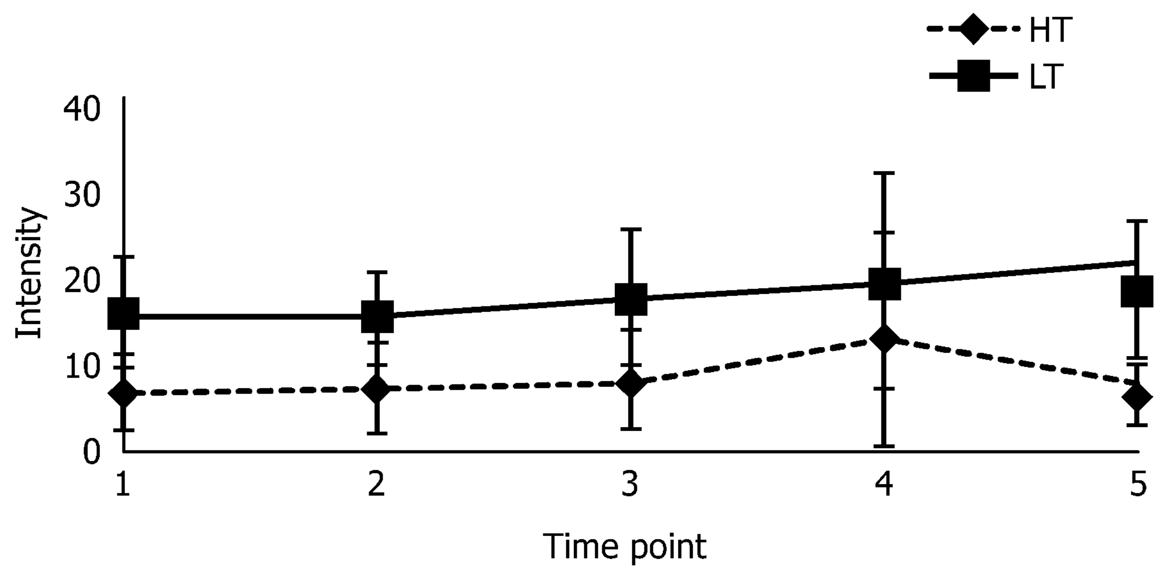

Referring to FIG. 3, five clusters with m/z values of 4478 Da, 6716 Da, 8293 Da, 8840 Da and 10571 Da were identified, based on data presented in the table of FIG. 3 (FIG. 3-I and FIG. 3II). The first cluster, 4478, is without overlapping standard deviations for high urinary toxicity versus low urinary toxicity at time points 2 and 4, as shown in FIG. 4A. The remaining clusters, 6716, 8293, 8840 and 10571, are without overlapping standard deviations at time point 5, as shown in FIGS. 4B-E, respectively. The most valuable cluster is the first one, allowing an early adaption of the treatment plan by the physician. Additionally, the two clusters with the m/z values of 8293 Da and 10571 Da show very good values for the three criteria (i.e., p-value, intensity difference and area under the ROC curve) at time point 1. Advantageously, this indicates that a radiosensitive patient can be identified before radiation therapy. This makes a prognosis of radiotoxicity and an individualization of the therapy before starting possible.

For the adaption of a radiotherapy plan, biomarkers of time point 2 are valuable. However, the time point 2 values are of limited reliability because of the small size of the HT patient group at this time point (i.e., two patients). The first cluster in FIG. 1 shows high intensity difference at time point 2. This could make an identification of sensitive patients at early stages of the radiation therapy possible and early modification of corresponding therapy plans possible. A combination of the markers of clusters 2-5, which have relatively large intensity differences at time point 1, would make a toxicity prognosis possible before the start of the radiation therapy.

On comparison of the data presented in the tables of FIGS. 1 and 3, it can be seen that the second clusters of both figures are very similar in mass (within a±0.2% interval of the mean mass). In this case, it could be that the underlying peptide is the same in both bowel and urinary toxicity, although the time dependence differs slightly.

Figure 5:
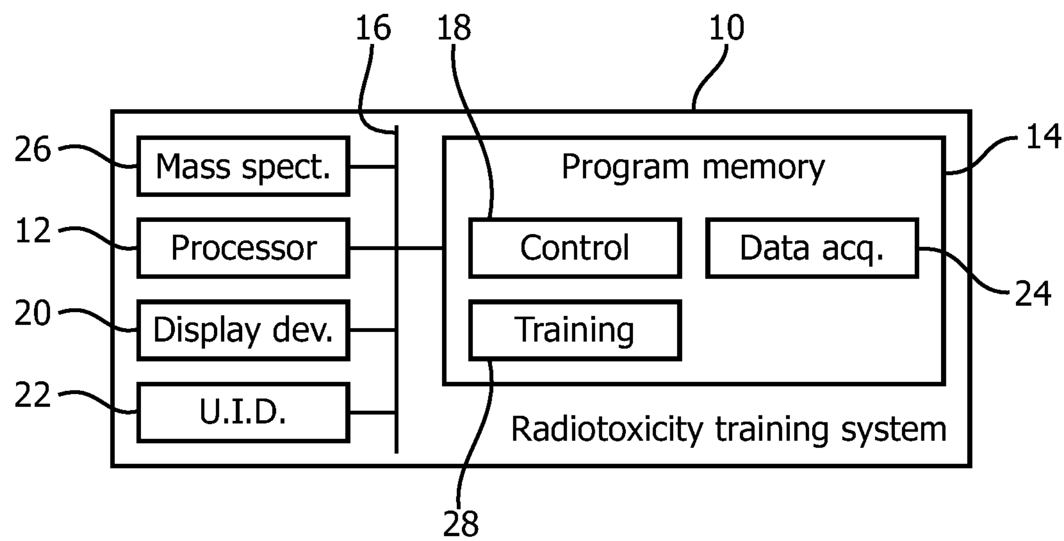
FIG. 5 illustrates a radiotoxicity training system.

With reference to FIG. 5, a radiotoxicity training system 10 determines biomarkers indicative of radiotoxicity caused by treatment of a disease, such as prostate cancer. The radiotoxicity training system 10 includes at least one processor 12 and at least one program memory 14. The program memory 14 includes processor executable instructions that, when executed by the processor 12, determine biomarkers indicative of radiotoxicity caused by treatment of the disease. The processor 12 executes the processor executable instructions to determine biomarkers indicative of radiotoxicity caused by treatment of the disease. The radiotoxicity training system 10 further includes at least one system bus 16 interconnecting the processor 12, the program memory 14, and any other components of the radiotoxicity training system 10.

A control module 18 of the processor executable instructions controls overall operation of the radiotoxicity training system 10, including determining biomarkers indicative of radiotoxicity caused by treatment of the disease. The control module 18 suitably displays a graphical user interface (GUI) to a user of the radiotoxicity training system 10 using a display device 20 of the radiotoxicity training system 10. Further, the control module 18 suitably allows the user to interact with the GUI using a user input device 22 of the radiotoxicity training system 10.

A data acquisition module 24 of the processor executable instructions acquires an MS data set of a urine sample of a patient using a mass spectrometer 26. The mass spectrometer 26 can be part of the radiotoxicity training system 10, as illustrated, or external thereto. Typically, the mass spectrometer 26 is a SELDI mass spectrometer. The MS data set captures a spectrum of biomarkers (e.g., in the peptide range) within the urine sample. The vertical axis of the spectrum corresponds to relative intensity and the horizontal axis of the spectrum corresponds to m/z. Typically, the MS data set is stored in a memory of the radiotoxicity training system 10. In preparing the urine sample for data acquisition, the urine sample is diluted to a predetermined protein concentration, such as 0.0251 g/L, so the MR data sets of different urine samples are comparable.

A training module 28 of the processor executable instructions determines a set of biomarkers to detect or predict radiotoxicity caused by treatment of the disease. This includes analyzing MS data sets of training urine samples of patients treated for the disease using radiation therapy to identify the biomarkers within the MS data sets which indicate radiotoxicity or susceptibility to radiotoxicity. The MS data sets are acquired using the data acquisition module 24.

In one embodiment, the clustering approach described above is employed to identify the set of biomarkers from the training MS data sets. That is to say, the peaks of the MS data sets for each combination of time point and class are clustered within a mass interval, such as ±0.2%. For example, the peaks of MS data sets for low urinary toxicity and a time point before radiation therapy are clustered. Peaks suitably include intensities exceeding a predetermined threshold, such as 15%.

Features of the clustered peaks are then extracted and analyzed to identify peaks which can discriminate between the classes (e.g., low urinary toxicity and high urinary toxicity). This includes, for each peak of a first class and of a time point, comparing the extracted features of the peak to the extracted features of a corresponding peak of a second, different class and of the time point to determine whether any of the features allow discrimination between the two classes. If a feature is found, a threshold for discriminating between the classes is determined thereby creating a classifier for the time point. Features include one or more of p-value, ROC-limit, and intensity.

The classifiers can be combined and, optionally, weighted based on discriminatory power to create a more reliable classifier of radiotoxicity and/or susceptibility to radiotoxicity. However, only classifiers for a time point before radiation therapy can be combined for determining a classifier for prediction of radiotoxicity.

In another embodiment, a machine learning routine is employed with a set of features corresponding to biomarkers within the MS data sets. The biomarkers are those with peaks found within the spectra captured by the MS data sets, where intensities of the peaks exceed a predetermined threshold, such as 15%. As above, the features can be one or more of p-values, ROC-limits and intensity differences of the peaks corresponding to the biomarkers. To select the features, a feature selection routine, such as a genetic algorithm, can be employed. Alternatively, a user of the radiotoxicity training system 10 can select the features. For example, all the features can be employed.

For each of the MS data sets, the set of features are extracted. Thereafter, the machine learning routine is applied to the extracted feature sets to generate a classifier to discriminate between classes. Classes include susceptible or unsusceptible, high toxicity or low toxicity, high urinary toxicity or low urinary toxicity, high bowel toxicity or low bowel toxicity, etc. Typically, the machine learning routine is a supervised machine learning routine. However, unsupervised and other types of machine learning routines are contemplated.

For assessing the susceptibility of the patient to radiotoxicity caused by treatment of the disease, training urine samples collected before radiation therapy are employed. In contrast, for determining radiotoxicity caused by treatment of the disease, training urine samples collected one or more of before, during and after radiation therapy are employed.

While the radiotoxicity training system 10 was described for a single disease, it is to be appreciated that it can be employed for multiple diseases. Namely, the foregoing training can be repeated by the training module 28 to identify biomarkers for radiation side effects of patients with other diseases, such as bladder, rectum, endometrial or cervix cancer.

Figure 6:
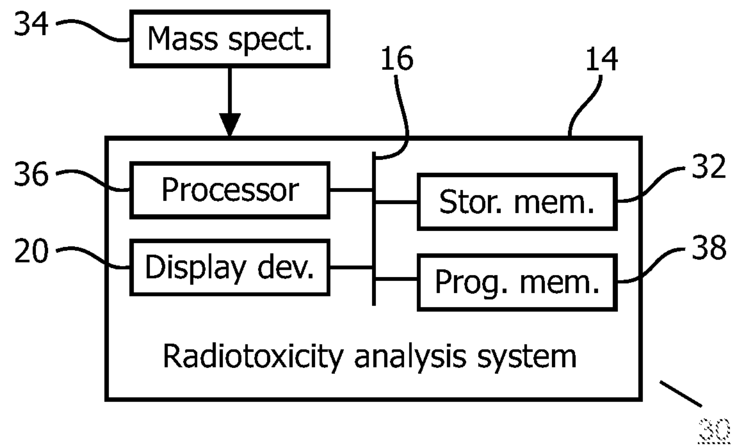
FIG. 6 illustrates a radiotoxicity analysis system.

With reference to FIG. 6, a radiotoxicity analysis system 30 monitors a patient for radiotoxicity, and/or susceptability to radiotoxicity, caused by treatment of a disease, such as prostate cancer. The radiotoxicity analysis system 30 finds particularly application in radiation therapy planning to reduce the risk of severe acute or chronic radiotoxicity. For example, an extra radiation dose boost to the target structures is beneficial for disease control, but may have to be left out in certain extra radiosensitive patients. Further, the radiotoxicity analysis system 30 allows timely personalization of the cancer therapy (e.g., in combination with chemotherapy and hormonal therapy).

The radiotoxicity analysis system 30 includes a storage memory 32. The storage memory 32 stores known biomarkers indicative of radiotoxicity, and/or susceptibility to radiation toxicity, caused by treatment of one or more diseases, including the disease. The known biomarkers can, for example, be determined by the radiotoxicity training system 10, discussed above. The corresponding classifiers for the biomarkers can also be stored in the storage memory 32.

In some embodiments, the radiotoxicity analysis system 30 includes a device 34 configured to determine biomarkers within a urine sample and to generate the data set. However, in other embodiments, the device 34 is external to the radiotoxicity analysis system 30, as illustrated. The device 34 can be a mass spectrometer, such as a SELDI mass spectrometer, or a device for reading (e.g., electronically) enzyme-linked immunosorbent assay (ELISA) on a microtiter plate or an electronic assay chip. The preparation of urine sample is suitably performed as recommended for the respective reader used.

The radiotoxicity analysis system 30 further includes at least one processor 36 and at least one program memory 38. The program memory 38 includes processor executable instructions that, when executed by the processor 36, monitor the patient for radiotoxicity, and/or susceptibility to radiotoxicity, caused by treatment of the disease. The processor 36 executes the processor executable instructions to monitor the patient for radiotoxicity, and/or susceptibility to radiotoxicity, caused by treatment of the disease. The radiotoxicity analysis system 30 further includes at least one system bus 40 interconnecting the processor 36, the program memory 38, and any other components of the radiotoxicity analysis system 30, such as a display device 42.

Figure 7:
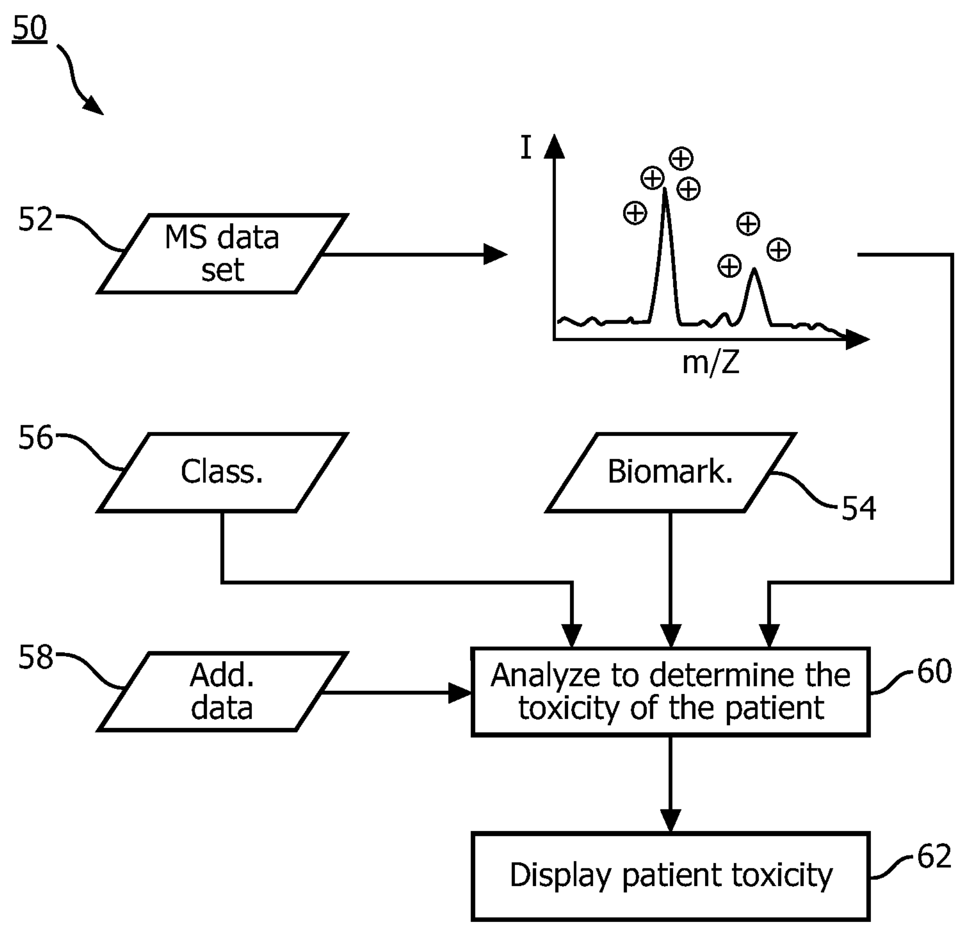
FIG. 7 illustrates a routine for monitoring a patient for radiotoxicity, and/or susceptability to radiotoxicity, caused by treatment of a disease.

To monitor the patient for radiotoxicity, and/or susceptibility to radiotoxicity, caused by treatment of the disease, the processor executable instructions of the program memory 38 implement the routine 50 of FIG. 7, such that the processor 36 is programmed to perform the routine 50 of FIG. 7. The routine 50 includes receiving a data set 52 (e.g., an MS data set or an ELISA assay measurement result, as illustrated) indicating the intensity (concentration) of biomarkers within a urine sample of the patient. The data set 52 can be received from, for example, the device 34.

The routine 50 also includes receiving biomarkers 54 indicative of radiotoxicity, or susceptibility to radiotoxicity, from treatment of the disease. The corresponding classifiers 56 for the biomarkers 54 can also be received. The biomarkers 54 and the classifiers 56 are suitably received from the storage memory 32, but can also be received from the radiotoxicity training system 10. Additional data 58 from one or more of genetic tests, tumor grading, scaling, histology, concurrent patient medication, patient file data, medical imaging, and in vitro diagnostics can also be obtained in order to obtain personalized information on disease and radiosensitivity. The additional data 58 can, for example, be received from a patient information system.

After receiving the foregoing data, the data set 52 is analyzed 60 to determine the toxicity of the patient. In some embodiments, this includes extracting the relevant features of the biomarkers 54. As noted above, for MS, the biomarkers 54 correspond to peaks in an MS spectrum, which are suitably defined as mass intervals. For example, the mass interval for a peak of a biomarker can be ±0.2% of the mean m/z of the peaks in all the patients used for training. It's important to use mass intervals because the spectra collected on different mass spectrometers differ slightly (e.g., due to imperfections in calibration). Also, the same MS peak identified in different subjects may present itself at slightly different m/z values. Such differences can be due to variation at various levels, including the genetic level and the post-translational modification level. Mass spectrometry, especially SELDI-MS, also has limited mass resolution.

Based on the extracted features, a determination is made as to whether the patient is suffering from radiotoxicity or whether the patient is susceptible to radiotoxicity. For example, the extracted features can be input into one of the classifiers 56 determined by, for example, the radiotoxicity training system 10. The determination can also be performed using the additional data 58 or a combination of both. A likelihood of the determination can also be made, for example, based on how close the extracted features are to thresholds.

The determination and/or the likelihood can then be displayed 62 to the user with the display device 42. A treating physician can then determine a treatment plan for the patient based thereon. For example, the treating physician can employ surgery, pure chemotherapy or hormone therapy instead of radiotherapy if the patient is highly radiosensitive. The determination can also be employed by other clinical decision making systems.

In some embodiments, the routine 50 analyzes the data set of a urine sample for bowel toxicity and urinary toxicity (types of radiotoxicity caused by the treatment of prostate cancer). As to bowel toxicity, the routine 50 analyzes the MS data of a urine sample acquired before radiation therapy for the 6732 Da biomarker and, based thereon, determines the susceptability of the patient to bowel toxicity. Further, in some embodiments, the routine 50 analyzes the MS data of a urine sample acquired after beginning radiation therapy for the 6732 Da and 2863 Da biomarkers and, based thereon, determines whether the patient is suffering or will later suffer from bowel toxicity.

As to urinary toxicity, the routine 50 analyzes the MS data of a urine sample acquired before radiation therapy for the 8293 Da and 10571 Da biomarkers and, based thereon, determines the susceptability of the patient to urinary toxicity. Further, in some embodiments, the routine 50 analyzes the MS data of a urine sample acquired before and/or after beginning radiation therapy for the 4478 Da, 6716 Da, 8293 Da, 8840 Da and 10571 Da biomarkers and, based thereon, determines whether the patient is suffering from urinary toxicity.

While the radiotoxicity analysis system 10 was described for a single disease, it is to be appreciated that it can be employed for multiple diseases. Namely, monitoring can be performed for the biomarkers of other diseases as well. Further, it is contemplated that the radiotoxicity training system 10 and the radiotoxicity analysis system 30 can be integrated. In such an embodiment, the confirmed classification of the patient as susceptible to radiotoxicity, or as suffering from radiotoxicity, can be used to update the classifiers 56.

Figure 8:
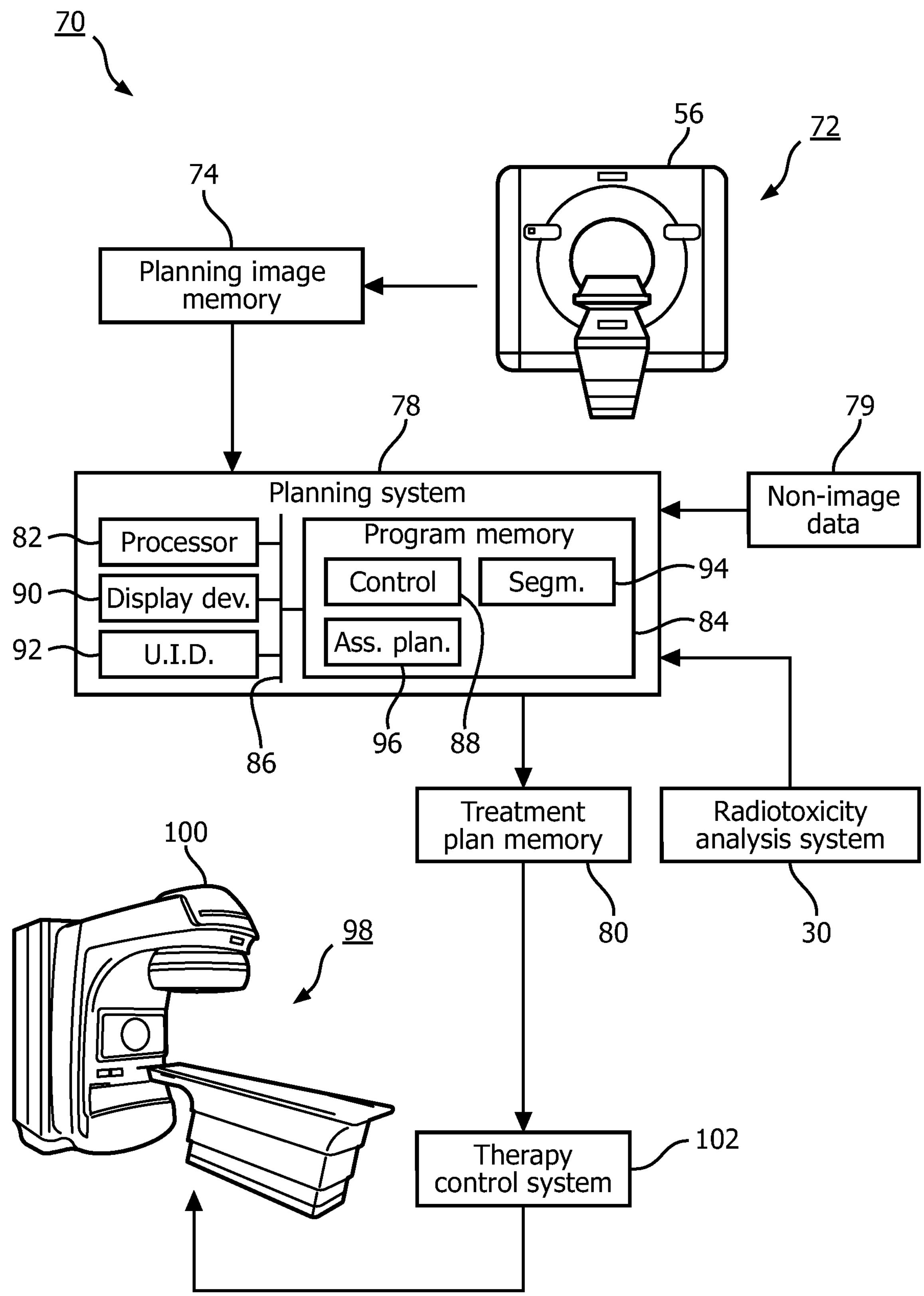
FIG. 8 illustrates a therapy system.

With reference to FIG. 8, a therapy system 70 includes an imaging system 72 to generate one or more planning images of a region of interest of a patient. The planning images are volumentric (i.e., three-dimensional) and typically stored in a planning image memory 74 of the therapy system 70. The region of interest includes one or more target structures and, typically, one or more critical structures. Each of the target structures is a lesion or other tissue region, such as a tumor, to be treated. Each of the critical structures is an organ or other tissue region which is at risk of damage from the radiation intended for the target structures, such as radiation traveling to the target structures, which has passed through the critical structures, or which passes closely adjacent the critical structures.

The imaging system 72 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 72 includes one or more scanners 76 corresponding to the imaging modalities, as well as a backend system reconstructing raw image data from the scanners into the planning images. As illustrated, the imaging system 72 generates the planning images using at least CT and includes a CT scanner 76.

A planning system 78 of the therapy system 70 generates and/or updates an optimal treatment plan for the patient using the planning images, which are typically received from the planning image memory 74, and/or non-imaging data 79. The planning system 78 can further use the radiotoxicity of the patient, and/or the susceptability of the patient to radiotoxicity, as determined by the radiotoxicity system. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 80 of the therapy system 70.

The planning system 78 includes at least one processor 82 and at least one program memory 84. The program memory 84 includes processor executable instructions that, when executed by the processor 82, generate and/or update the optimal treatment plan. The processor 82 executes the processor executable instructions to generate and/or update the optimal treatment plan. The planning system 78 further includes at least one system bus 86 interconnecting the processor 82, the program memory 84, and any other components of the planning system 78.

A control module 88 of the processor executable instructions controls overall operation of the planning system 78, including generating and/or updating of the optimal treatment plan. The control module 88 suitably displays a graphical user interface (GUI) to a user of the planning system 78 using a display device 90 of the planning system 78. Further, the control module 88 suitably allows the user to interact with the GUI using a user input device 92 of the planning system 78. For example, the user can interact with the GUI to specify parameters controlling the generating and/or update of the optimal treatment plan.

A segmentation module 94 of the processor executable instructions segments the planning images to identify the boundaries of the structures (i.e., the target structures and, typically, the critical structures) within the planning images. The segmentation can be performed automatically and/or manually. As to automatic segmentation, a segmentation routine is employed to identify the boundaries of the structures. The segmentation routine can be one of any number of known segmentation routines, such as a model or atlas based segmentation routine. As to manual segmentation, a user uses the user input device 92 to identify the boundaries of the structures. In some embodiments, the segmentation module 94 employs the user interface to display the planning images to the user. The user can then identify the boundaries of the structures on the planning images using the user input device 92.

It is also contemplated that the segmentation can be performed using a combination of automatic and manual segmentation. Namely, the boundaries of the structures can be automatically identified as described above. The automatically identified boundaries can then be displayed to the user, optionally overlaid on the planning images, using the display device 90 and the user can modify the identified boundaries, as necessary, using the user input device 92.

An assisted planning module 96 of the processor executable instructions generates and/or updates the optimal treatment plan. This includes receiving input parameters for generation of the treatment parameter. The input parameters include the boundaries of the structures (i.e., the target structures and, typically, the critical structures) within the planning images, which are identified using the segmentation module 94. The input parameters further include parameters received from the user input device 92. These parameters include labeling each of the structures identified in the planning images as one of a target structure and a critical structure. Further, these parameters include, for each structure, specification of a dose profile to be achieved based on the user's expertise or clinical guidelines.

The input parameters can further include the radiotoxicity of the patient, and/or the susceptability of the patient to radiotoxicity, as determined by the radiotoxicity analysis system 30 of FIG. 6. This advantageously permits modification of the optimal treatment plan to reduce the risk of chronic or severe acute radiotoxicity. For example, an extra radiation dose boost to the target structures is beneficial for disease control, but may have to be left out in certain extra radiosensitive patients. As another example, if the patient starts showing signs of radiotoxicity during treatment (i.e., molecular signs (=changes in peptide concentrations), before clinical symptoms of radiotoxicity appear), the optimal treatment plan can be updated to reduce the radiation dose.

Based on the input parameters, the assisted planning module 96 generates and/or updates the optimal treatment plan according to an inverse treatment planning routine. Any number of well-known routines can be employed. However, in general, the inverse treatment planning routine seeks to minimize the dose to critical structures, while achieving a uniform, ideal dose to the target structures. The optimal treatment plan is typically stored in a treatment plan memory 80 of the therapy system 70.

A delivery system 98 executes the optimal treatment plan to deliver therapy, such as ablation therapy, external beam radiation therapy and/or brachytherapy, to the patient. The therapy typically includes radiation, such as one or more of x-rays, gamma rays, protons, high-intensity focused ultrasound (HIFU), and the like. The delivery system 98 includes a delivery apparatus 100, such as a linear particle accelerator, and a control system 102, which controls the delivery apparatus 100 in accordance with the optimal treatment plan. The optimal treatment plan is typically received from the treatment plan memory 80, but other sources are contemplated.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for treatment of toxicity induced by radiation therapy, said method comprising:

receiving a urine sample from a human subject; and, detecting whether one or more biomarkers are present in the urine sample by performing a mass spectrometry (MS) analysis of the urine sample, wherein the one or more biomarkers are selected from the group consisting of polypeptides having a mass of 4478±9 Da, 6716±13 Da, 8293±17 Da, 8840±18 Da, 10571±21 Da, 2863±6 Da and 6732±13 Da;

determining or predicting radiation toxicity in the human subject when the one or more biomarkers are detected by the MS analysis within the urine sample;

modifying the radiation therapy administered to the human subject based on the determined or predicted radiation toxicity;

generating or updating a radiation treatment plan, wherein doses are reduced in response to toxicity or in response to susceptibility to toxicity detected from the patient, the radiation treatment plan including a plurality of treatment fractions, each treatment fraction identifying planning target volumes (PTVs) for a target structure of the patient, margins around the target structure, dose profiles for the target structure, and dose limits for a critical structure of the patient; and reducing a dose of the radiation therapy administered to the human subject based on the determined or predicted radiation toxicity in accordance with the radiation treatment plan.

2. The method according to claim 1, wherein the one or more biomarkers are selected from the group consisting of polypeptides having a mass of 2863±6 Da and 6732±13 Da, wherein the radiation toxicity is a bowel toxicity caused by the radiation therapy.

3. The method according to claim 1, wherein the radiation therapy is a radiation therapy of prostate cancer, and the one or more biomarkers have a mass of 6732±13 Da when the radiation toxicity is a bowel toxicity induced by the radiation therapy of the prostate cancer.

4. The method according to claim 1, wherein the one or more biomarkers are selected from the group consisting of polypeptides having a mass of 4478±9 Da, 6716±13 Da, 8293±17 Da, 8840±18 Da, and 10571±21 Da, when the radiation toxicity is a urinary toxicity caused by the radiation therapy.

5. The method according to claim 1, wherein the radiation therapy is a radiation therapy of prostate cancer, and wherein the one or more biomarkers are selected from the group consisting of polypeptides having a mass of 8293±17 Da and 10571±2.1 Da, when the radiation toxicity is a urinary toxicity induced by the radiation therapy of the prostate cancer.

6. The method according to claim 1, wherein the determining or predicting further uses data from one or more of genetic tests, tumor grading, scaling, histology, concurrent patient medication, patient file data, medical imaging, or in vitro diagnostics.

7. The method of claim 1, wherein the mass spectrometry analysis is performed by a Surface-Enhanced Laser Desorption/Ionization (SELDI) mass spectrometer.

* * * * *